(12) United States Patent
Small et al.

(10) Patent No.: US 9,101,708 B2
(45) Date of Patent: Aug. 11, 2015

(54) POWERHEAD CONTROL IN A POWER INJECTION SYSTEM

(75) Inventors: James R. Small, Beavercreek, OH (US);
David M. Brooks, Cincinnati, OH (US);
Charles S. Neer, Cincinnati, OH (US);
Frank M. Fago, Mason, OH (US)

(73) Assignee: LIEBEL-FLARSHEIM COMPANY LLC, Hazelwood, MO (US)

( * ) Notice: Subject to any disclaimer, the term of this patent is extended or adjusted under 35 U.S.C. 154(b) by 923 days.

(21) Appl. No.: 11/073,910

(22) Filed: Mar. 7, 2005

(65) Prior Publication Data
US 2006/0079768 A1 Apr. 13, 2006

Related U.S. Application Data

(62) Division of application No. 10/964,002, filed on Oct. 13, 2004, now abandoned.

(51) Int. Cl.
*A61M 5/145* (2006.01)
*A61M 5/00* (2006.01)
(Continued)

(52) U.S. Cl.
CPC ........... *A61M 5/14546* (2013.01); *A61M 5/007* (2013.01); *A61M 5/14566* (2013.01); *A61M 5/16827* (2013.01); *A61M 5/172* (2013.01);
(Continued)

(58) Field of Classification Search
CPC .................. A61M 5/14546; A61M 2205/3561; A61M 2205/3362; A61M 2205/505; A61M 2205/6081
USPC ........... 604/131, 151, 152, 154; 600/431, 432
See application file for complete search history.

(56) References Cited

U.S. PATENT DOCUMENTS 4,483,342 A * 11/1984 Pfeifer .......................... 600/425
5,423,750 A * 6/1995 Spiller ............................ 604/80
(Continued)

FOREIGN PATENT DOCUMENTS

EP 0 192 786 9/1986
EP 1 449 550 8/2004
(Continued)

OTHER PUBLICATIONS

E-Z-EM, Inc., *Empower/CT, EmpowerCTA—E-Z-EM Injectors Empower Your CT Scanner*, Product Brochure, Rev. Nov. 2003, 8 pages.
(Continued)

*Primary Examiner* — Andrew Gilbert
(74) *Attorney, Agent, or Firm* — Marsh Fischmann & Breyfogle LLP

(57) ABSTRACT

A dual head contrast media injection system performs a patency check or test injection, determining flow rate and/or flow volume from the programmed protocol. The tubing that connects syringes to a patient shares only a short common section near to the patient. Appropriate injection steps are taken to compensate for tubing elasticity. A wireless remote control and a touch screen control are provided, improving functionality and information delivery. The display brightness is controlled based on the ambient light, and the display panel includes a double swivel permitting re-orientation. The orientation of the display may also be controlled based on, e.g., the current step, the tilt angle of the powerhead, or a manual control. Furthermore, the display is customizable to identify the type of fluid (contrast, saline, etc.) on either side of the injector, to provide matched color coding, and to provide a folder/tab analogy for retrieving injection protocol parameters.

7 Claims, 10 Drawing Sheets

(51) Int. Cl.
  *A61M 5/168* (2006.01)
  *A61M 5/172* (2006.01)
  *A61M 39/10* (2006.01)

(52) U.S. Cl.
  CPC ........ *A61M 39/10* (2013.01); *A61M 2205/3362* (2013.01); *A61M 2205/3523* (2013.01); *A61M 2205/3561* (2013.01); *A61M 2205/3592* (2013.01); *A61M 2205/50* (2013.01); *A61M 2205/505* (2013.01); *A61M 2205/6081* (2013.01)

(56) References Cited

U.S. PATENT DOCUMENTS

| | | | |
|---|---|---|---|
| 5,573,515 A * | 11/1996 | Wilson et al. | 604/236 |
| 5,728,074 A | 3/1998 | Castellano et al. | 604/207 |
| 5,814,015 A * | 9/1998 | Gargano et al. | 604/67 |
| 5,868,710 A | 2/1999 | Battiato et al. | |
| 5,925,022 A * | 7/1999 | Battiato et al. | 604/208 |
| 5,935,099 A | 8/1999 | Peterson et al. | |
| 6,450,963 B1 | 9/2002 | Ackerman | 600/459 |
| 6,482,185 B1 | 11/2002 | Hartmann | 604/189 |
| 6,533,757 B1 | 3/2003 | Lampropoulos et al. | 604/131 |
| 6,572,585 B2 | 6/2003 | Choi | 604/131 |
| 6,643,537 B1 | 11/2003 | Zatezalo et al. | |
| 6,673,033 B1 | 1/2004 | Sciulli et al. | |
| 6,689,091 B2 | 2/2004 | Bui et al. | 604/67 |
| 6,997,905 B2 | 2/2006 | Gillespie, Jr. et al. | |
| 7,169,135 B2 | 1/2007 | Duchon et al. | |
| 2001/0047153 A1 | 11/2001 | Trocki et al. | |
| 2002/0151804 A1 | 10/2002 | O'Mahony et al. | |
| 2002/0183616 A1 | 12/2002 | Toews et al. | |
| 2003/0216643 A1 | 11/2003 | Zatezalo et al. | |
| 2004/0064041 A1 * | 4/2004 | Lazzaro et al. | 604/152 |
| 2004/0162484 A1 | 8/2004 | Nemoto | |
| 2004/0223007 A1 | 11/2004 | Mamata | |
| 2005/0113754 A1 | 5/2005 | Cowan | |
| 2005/0182323 A1 | 8/2005 | Grispo et al. | |
| 2006/0184122 A1 * | 8/2006 | Nemoto | 604/154 |
| 2007/0083152 A1 * | 4/2007 | Williams et al. | 604/65 |
| 2007/0093712 A1 * | 4/2007 | Nemoto et al. | 600/432 |
| 2007/0276327 A1 | 11/2007 | Kalafut et al. | |

FOREIGN PATENT DOCUMENTS

| | | |
|---|---|---|
| JP | 2001505104 | 4/2001 |
| JP | 2003505211 | 2/2003 |
| JP | 2004-504912 | 2/2004 |
| JP | 2004248734 | 9/2004 |
| JP | 2004-279503 | 10/2004 |
| WO | 9822168 | 5/1998 |
| WO | 00/64353 | 11/2000 |
| WO | 0108730 | 2/2001 |
| WO | 02/11049 | 2/2002 |

OTHER PUBLICATIONS

E-Z-Em, Inc., *EmpowerCT \*\*Industrial Design Excellence Award Winner\*\**, Product Webpage, © 1993-2005, 3 pages.

E-Z-Em, Inc., *EmpowerCT, EmpowerCTA, IrisCT, CT Injector Reporting Information System*, Product Power Point Slides Presentation, 11 Pages.

E-Z-EM, Inc., *Injector Systems Marking Bulletin*, Memorandum to Global Sales Organization, Nov. 22, 2004, 1 page.

Birnbaum et al., *Extravasation Detection Accessory; Clinical Evaluation of 500 Patients*, Radiology 1999; 212:431-438, 2 Page Summary.

Schoept, *Clinical Applications of Saline Bolus Chasing Techniques with the E-Z-EM Double Syringe Injection System for Contrast-Enhanced Multidetector-Row CT Angiography; CT Coronary Angiography*, Technical Note by E-Z-EM, Inc., Sep. 2004, 2 pages.

Medrad Inc., *MEDRAD Avanta™ Fluid Management Injection System*, Product Webpage, Printed Mar. 4, 2005, 2 pages.

Medrad Inc.. *MEDRAD Avanta™ Fluid Management Injection System*, Product Webpage, Printed Jun. 21, 2005, 2 pages.

Medrad Inc., *When it Comes to Reliability, We've Made Quite a Mark, Mark V ProVis™ the latest generation of injection systems from Medrad®*, Product Brochure, © 1999, 4 pages.

Medrad Inc., *IV Infusion for MRI Just Got Better CONTINUUM MR Compatible Infusion System*, Product Brochure, © 2004, 2 pages.

Medrad Inc., *A Dedicated Dual-Head CT Injection System, Stellant™ CT Injection Systems*, Product Flyer, 1 page.

Medrad Inc., *MEDRAD CT, Visualize the whole heart with DualFlow, our latest innovation for the Stellant D. Stellant® CT Injection Systems*, Product Brochure, © 2004, 2 pages.

Medrad Inc., *Stellant™ CT Injection Systems Your Intelligent, Total Fluid Delivery System*, Product Brochure, © 2004, 4 pages.

Gridley et al., *Significant Reduction of Contrast Dose in Chest CT Angiography Utilizing a Dual Injection System with Saline Flush*, Medrad CT Clinical Information, © 2003, 1 page.

Haage et al., *Reduction of Contrast Material Dose and Artifacts by a Saline Flush Using a Double Power Injector in Helical CT of the Thorax*, AJR:174, Apr. 2000, 1049-1053.

Tecnovate Pty Ltd., *Aquaject, Dual Barrel Contrast Injector for CT or MRI*, Coming Soon Flyer, 1 page.

\* cited by examiner

| | | Phase | Side | ml/sec | ml | sec | Phase | Side | ml/sec | ml | sec |
|---|---|---|---|---|---|---|---|---|---|---|---|
| 222 | proto1 | 1<br>3<br>5 | A<br>- | 1.0 | 75 | 13 | 2<br>4<br>6 | B | 2.0 | 18 | 12 |
| 222 | Dr Jim | 1<br>3<br>5 | A<br>A<br>- | 7.0<br>3.0 | 75<br>14 | 13<br>600 | 2<br>4<br>6 | B<br>A | 2.0<br>4.0 | 18<br>18 | 12<br>600 |
| 222 | LIVER | 1<br>3<br>5 | A<br>- | 1.0 | 75 | 13 | 2<br>4<br>6 | B | 2.0 | 18 | 12 |
| 222 | 3 | 1<br>3<br>5 | A<br>A | 1.0<br>3.0 | 75<br>14 | 13<br>600 | 2<br>4<br>6 | B<br>- | 2.0 | 18 | 12 |
| 222 | AAAAAAAABBBBBCCCC | 1<br>3<br>5 | A<br>A<br>- | 5.0<br>3.0 | 75<br>14 | 13<br>600 | 2<br>4<br>6 | B<br>A | 2.0<br>4.0 | 18<br>18 | 12<br>600 |
| 222 | PROTOCL 2 | 1<br>3<br>5 | A | 1.0 | 75 | 13 | 2<br>4<br>6 | - | | | |
| 222 | 44444 | 1<br>3<br>5 | A<br>A<br>- | 6.0<br>3.0 | 75<br>14 | 13<br>600 | 2<br>4<br>6 | B<br>A | 2.0<br>4.0 | 18<br>18 | 12<br>600 |
| 222 | | 1<br>3<br>5 | | | | | 2<br>4<br>6 | | | | |
| Memory | | 1<br>3<br>5 | A | 1.0 | 75 | 13 | 2<br>4<br>6 | - | | | |

Move | Delete | Edit Name | Store

1 | 2 | 3 | 4 | 5 | Main
224 | 224 | 224 | 224 | 224

FIG. 4E

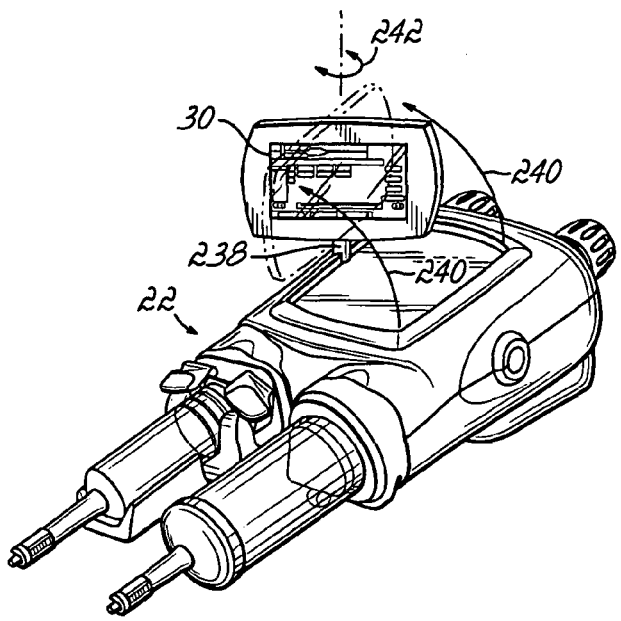

FIG. 4F

POWERHEAD CONTROL IN A POWER INJECTION SYSTEM

CROSS REFERENCE TO RELATED APPLICATIONS

The present application is a divisional application of U.S. application Ser. No. 10/964,002, filed Oct. 13, 2004, entitled POWERHEAD OF A POWER INJECTION SYSTEM, now abandoned, which is related to application Ser. No. 10/964, 003, filed Oct. 13, 2004, entitled POWER.HEAD OF A POWER INJECTION SYSTEM, now U.S. Pat. No. 7,507, 221. The present application is related to co-pending and concurrently filed application Ser. No. 11/073,915, entitled POWERHEAD OF A POWER INJECTION SYSTEM, now abandoned, and the two divisional applications of application Ser. No. 10/964,003, filed Oct. 13, 2004, entitled POWERHEAD OF A POWER INJECTION SYSTEM, now U.S. Pat. No. 7,507,221. All of these applications are hereby incorporated by reference herein in their entirety.

FIELD OF THE INVENTION

The present invention relates to contrast media injector systems and, more particularly to improvements thereto.

BACKGROUND OF THE INVENTION

In many medical environments, a medical fluid is injected into a patient during diagnosis or treatment. One example is the injection of contrast media into a patient to improve CT, Angiographic, Magnetic Resonance or Ultrasound imaging, using a powered, automatic injector.

Injectors suitable for these and similar applications typically must use a relatively large volume syringe and be capable of producing relatively large flow rates and injection pressures. For this reason, injectors for such applications are typically motorized, and include a large, high mass injector motor and drive train. For ease of use, the motor and drive train are typically housed in an injection head, which is supported by a floor, wall, or ceiling mounted arm.

The injection head is typically mounted on the arm in a pivotal manner, so that the head may be tilted upward (with the syringe tip above the remainder of the syringe) to facilitate filling the syringe with fluid, and downward (with the syringe tip below the remainder of the syringe) for injection. Tilting the head in this manner facilitates removal of air from the syringe during filling, and reduces the likelihood that air will be injected into the subject during the injection process. Nevertheless, the potential for accidentally injecting air into a patient remains a serious safety concern.

In addition to the injection head discussed above, many injectors include a separate console for controlling the injector. The console typically includes programmable circuitry which can be used for automatic, programmed control of the injector, so that the operation of the injector can be made predictable and potentially synchronized with operations of other equipment such as scanners or imaging equipment.

Thus, at least part of the injection process is typically automatically controlled; however, the filling procedure, and typically some part of the injection procedure, are normally performed by an operator, using hand-operated movement controls on the injector head. Typically, the hand-operated movement controls include buttons for reverse and forward movement of the injector drive ram, to respectively fill and empty the syringe. In some cases, a combination of buttons is used to initiate movement of the ram or to control ram movement speed. The injector head also typically includes a gauge or display for indicating injection parameters to the operator, such as the syringe volume remaining, for the operator's use when controlling the injector head. Unfortunately, operators have found it cumbersome to use the hand-operated movement buttons and to read the injector head gauges and displays, for several reasons, not the least of which is the necessary tilting of the injector head between the upward, filling position to the downward, injection position, changing the positions of the hand-operated movement buttons relative to the operator, and at some tilt angles rendering the gauges or displays difficult to read.

In many applications, it is desirable to use an injector with multiple different syringe sizes. For example, it may be desirable to use a smaller syringe for pediatric use than for adult use, or where a particular procedure requires a smaller volume of fluid. To facilitate the use of different syringe sizes, injectors have been constructed with removable faceplates, where each of the various faceplates is configured for a particular syringe size. Typically, the injector is able to adjust injection parameters by detecting which faceplate is mounted to the injector, for example using a magnetic detector mounted to the front surface of the injector housing to detect the presence or absence of a magnet in the faceplate. Unfortunately, the necessity of incorporating a magnetic detector into the outer housing of the injector head increases the complexity and expense of manufacturing the injector head.

Recently, one development in power injectors has been the introduction of dual headed injectors, that is, an injector with two drive systems and mountings for two syringes. The software for the injector provides for independent control of these drive systems using both manual controls and programmed injection routines in response to a stored sequence. Such dual headed injectors allow multiple fluids to be injected during a sequence without changing a syringe or other equipment.

Regardless of the benefits of current power injector systems, whether single head or dual head, improvements and advances in this field continue to be desirable goals and will ensure that such equipment becomes easier to use, increase in functionality, and become more reliable and efficient in operation.

SUMMARY OF THE INVENTION

Accordingly embodiments of the present invention relate to improving power injectors that are used to inject contrast media and other fluids in a patient or animal.

One aspect of the present invention relates to a display, such as the console or powerhead, of the injector system accommodating different ambient light conditions. For example, the display elements such as LCD screens and LED lights can be controlled such that their relative brightness levels are dependent on the ambient light conditions. Operator override functionality can be provided as well.

Another aspect of the present invention relates to a touch screen interface for the powerhead of the contrast media injector system. The touch screen display can be driven from software so that it is configurable and not dependent on hardwired switches, LED indicators or 7-segment displays. The powerhead can therefore, provide the same functionality as the console display, thereby eliminating the console if desired. In addition to more data and more controls being available at the powerhead, help instructions and other contextual assistance can be provided to help the operator run the equipment.

Yet another aspect of the present invention relates to a display for a dual head injector system that displays information about both syringes and fluid simultaneously. The display of the powerhead is color-coded so that information about one syringe is visually distinct from information about the other syringe. For additional ease-of-use conventional color associations can be used such that a purple display refers to contrast media, yellow refers to saline, and black refers to air.

In accordance with another aspect, additional ease-of-use features are included in the display of stored protocol information, by use of a folder-tab analogy for managing numerous stored protocols.

Still a further aspect of the present invention relates to a remote controlled powerhead. A conventional powerhead drive mechanism and syringes are augmented to include a receiver for receiving a control signal from a remote device. In response to the control signal, the powerhead operates the syringe ram appropriately.

One additional aspect of the present invention relates to a dual head injector that utilizes tubing in which the fluid paths remain separate until substantially at the patient. By utilizing this type of V-tubing, the elasticity of the fluid delivery components (e.g., syringe, tubing, etc.) can be easily accommodated and there is reduced lag time in administration of a desired fluid to a patient.

One more aspect of the present invention relates to performing a patency check using a dual head injector system. In accordance with this aspect of the invention, a saline injection is enabled and performed prior to execution of the stored protocol of an injection, at nearly the same flow rate and volume as the upcoming media injection, to ensure that extravasation does not occur. This method may be implemented in software that retrieves the flow rate and other information about a selected protocol and controls the saline patency injection based on those parameters.

A related aspect of the present invention relates to a test injection feature. In accordance with this aspect, a test injection is performed, initially using the same fluid and initial flow rate as an stored protocol of an injection, to enable the user to determine the suitability of that flow rate and also determine the timing associated with the injection such as the delay time for the injected fluid to reach an area of interest of the patient.

It will be appreciated that both the test injection and patency check have common characteristics that distinguish them from normal programming of an injector. Specifically, both are an injection that is separately enabled from the stored injection protocol to be administered to the patient, and both are separate from the stored injection protocol, i.e., they may selectively be conducted, or not, at the operator's discretion. Thus, the operator need not perform a patency check or test injection, but has the ready option to do so without altering a stored injection protocol. While the patency check and test injection are thus functionally and operationally separated from a stored protocol, they are nevertheless programmatically controlled injections, and use parameters that may be derived from the later, stored injection protocol, e.g., the flow rates or use of fluids is modeled after the planned injection. Because the test injection and patency check are programmatically controlled injections, they may accurately mimic the stored injection protocol in the relevant aspects, without the effort of human involvement and the possibility for human error. Furthermore, because they are programmatically controlled, it is possible to calculate the fluid requirements of the patency check or test injection, which may be combined with the planned subsequent injection to ensure that there is sufficient injectable fluid available, thus ensuring that time is not lost re-filling the injector (which may involve re-entering the scanning room after it has been sealed) as may occur if a patency check or test injection is manually performed. Finally, in the context of a dual headed injector, a test injection or patency check, because it is programmatically controlled, may include functionality to automatically return the injector tubing to an appropriate initial state, e.g., a state in which the tubing is filled with saline or contrast media, or a mixture, as the operator and physician prefers for the imaging procedure.

Another aspect of the present invention relates to a mount for a display screen on an injector that permits the screen to be positioned flush with a surface of the injector or to be moved to a position extending from the surface of the injector. In the described embodiment the mount provides a double swivel permitting the screen to be swivelled away from the injector surface and pivoted about its axis, thereby facilitating visibility of the screen for numerous possible injector and operator positions.

A related aspect of the present invention involves programming of the powerhead to orient the content on the display automatically to an appropriate orientation and/or re-size that content based upon the current step in an injection sequence. This aspect may also be combined with sensors relating to the orientation of the display. For example, if a sensor is included in the mounting mentioned above, the display may be automatically re-oriented in response to tilting of the display away from the injector. Further, if an Earth gravitation sensor is included in the injector, the display may be automatically re-oriented in response to tilting of the injector relative to gravity, e.g. tilting upward for filling and downward for injecting.

A further aspect of the present invention relates to an injector powerhead for injection from first and second syringes, which may contain fluids of two different types, in which the injector permits an operator to identify the type of fluid contained in the first or the second syringe, thus enabling the operator to use either syringe location for either type of fluid, at the operator's discretion.

It will be appreciated that principles of the present invention are applicable to the injection of contrast media into a patient to improve CT, Angiographic, Magnetic Resonance or Ultrasound imaging, or any other application involving injection of fluids using a powered, automatic injector.

The above and other objects and advantages of the present invention shall be made apparent from the accompanying drawings and the description thereof.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

FIGS. 4A-4E illustrate a series of exemplary interface screens for a touch-screen display of a powerhead in accordance with the principles of the present invention.

FIG. 4F illustrates a swivel mount for an injector powerhead display screen in accordance with principles of the present invention.

DETAILED DESCRIPTION OF SPECIFIC EMBODIMENTS

Figure 1A:
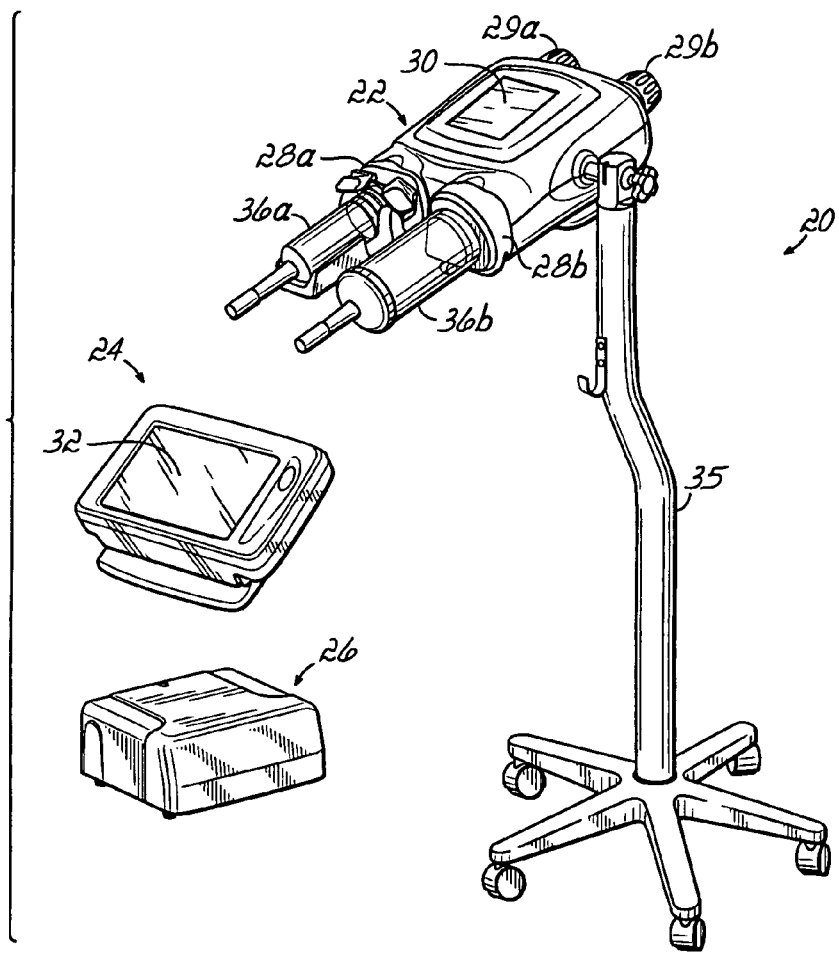
FIG. 1A illustrates a power injector system according to the principles of the present invention.

Referring to FIG. 1A, an injector 20 in accordance with the present invention includes various functional components, such as a powerhead 22, a console 24 and powerpack 26. Syringes 36a and 36b are mounted to the injector 20 in faceplates 28a and 28b of the powerhead 22, and the various injector controls are used to fill the syringe with, e.g., contrast media for a CT, Angiographic or other procedure, which media is then injected into a subject under investigation under operator or pre-programmed control.

The injector powerhead 22 includes a hand-operated knobs 29a and 29b for use in controlling the movement of the internal drive motors engaged to syringes 36a and 36b, and a display 30 for indicating to the operator the current status and operating parameters of the injector. The console 24 includes a touch screen display 32 which may be used by the operator to remotely control operation of the injector 20, and may also be used to specify and store programs for automatic injection by the injector 20, which can later be automatically executed by the injector upon initiation by the operator.

Powerhead 22 and console 24 connect through cabling (not shown) to the powerpack 26. Powerpack 26 includes a power supply for the injector, interface circuitry for communicating between the console 24 and powerhead 22, and further circuitry permitting connection of the injector 20 to remote units such as remote consoles, remote hand or foot control switches, or other original equipment manufacturer (OEM) remote control connections allowing, for example, the operation of injector 20 to be synchronized with the x-ray exposure of an imaging system.

Powerhead 22 is mounted to a wheeled stand 35, which includes a support arm for supporting powerhead 22 for easy positioning of powerhead 22 in the vicinity of the examination subject. Console 24 and powerpack 26 may be placed on a table or mounted on an electronics rack in an examination room. Other installations are also contemplated however; for example, powerhead 22 may be supported by a ceiling, floor or wall mounted support arm.

Figure 1B:
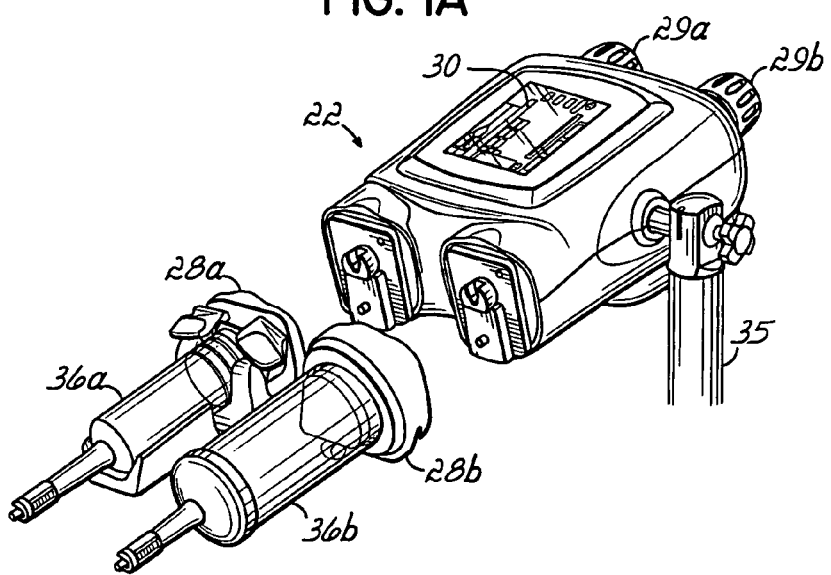
FIG. 1B illustrates the components of the powerhead of that system.

Referring to FIG. 1B, details of the powerhead 22 can be seen. In FIG. 1B, specific content can be seen on touch screen display 30 illustrating the two syringes and their status, as well as a protocol of injection steps to be used in conjunction with those two syringes.

Although the powerhead 22 discussed herein is a dual head injector, embodiments of the present invention explicitly contemplated single head injectors as well.

Figure 2:
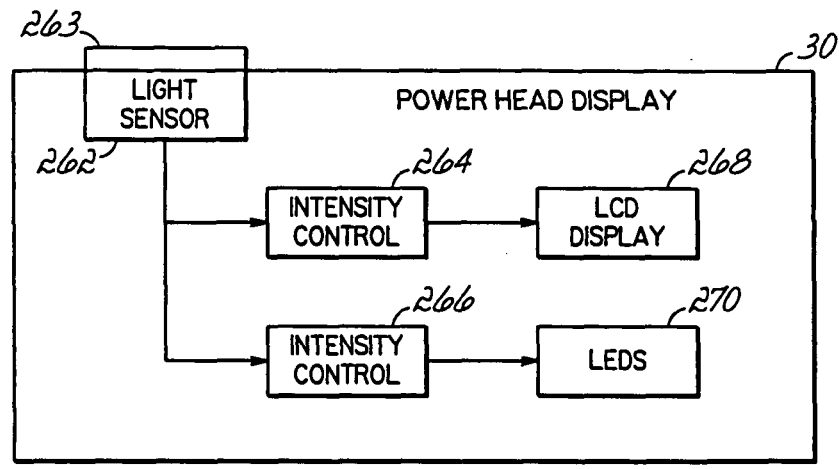
FIG. 2 illustrates a block diagram of a display system that controls the brightness of its display elements based on ambient light conditions in accordance with the principles of the present invention.

Referring to FIG. 2, an optical sensor 262 is included on one of the internal circuit boards within the injector powerhead housing 30 and is situated near a window 263 or other opening that allows it to detect ambient light levels. Such an optical sensor 262 would typically be an analog device that converts the light level detected into a voltage or current signal. After being converted via an analog-to digital converter (ADC), this signal could then be used by a microprocessor to raise or lower the brightness levels of the display. The control algorithm for correlating detected light levels with a display brightness setting may be selected according to a variety of methods. For example, the brightness and detected light levels may be linearly correlated. However, if the optical sensor 262 has a non-linear detection curve then an appropriate correlation formula can be used to change the brightness levels. Additionally, the brightness changes might occur at a limited number of predefined steps or, alternatively, cover a nearly-continuous spectrum of brightness settings. Thus, one of ordinary skill would recognize that within the scope of the present invention, there are a variety of functionally equivalent methods for adjusting the brightness of the power injector's display based on the ambient light conditions.

The methods of adjusting the brightness vary with the type of display. For example, brightness of LED's 270 on the powerhead may be adjusted by adjusting the duty cycle of the signal driving the LED. An LCD driver circuit 268, on the other hand, could use a pulse-width modulated signal, or a DC voltage level, to control its brightness setting. The intensity control circuits 264, 266, therefore, may be different depending on the type of display (e.g., 268, 270) being controlled.

Figure 3:
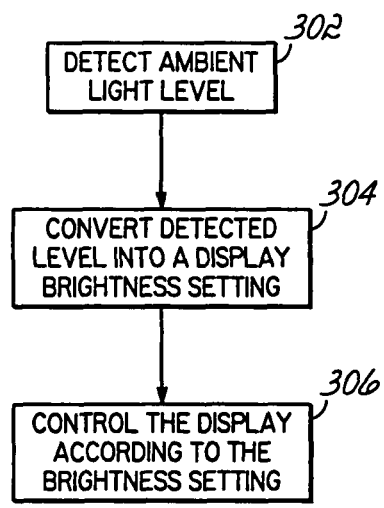
FIG. 3 depicts a flowchart of an exemplary algorithm useful with the system of FIG. 2.

An exemplary algorithm for controlling the display of either the powerhead 30 or the console 32 is depicted in the flowchart of FIG. 3. The sensors and control circuitry are conventional in nature and one of ordinary skill will recognize that a variety of functionally equivalent circuits could be used to generate the appropriate control signals. In step 302, a sensor is used to detect an ambient light level in the environment where the injector equipment is being used. Then, in step 304, this detected level is converted into a brightness setting for the display. This conversion process may include simple analog-to digital circuitry or use a microprocessor with accessible memory that correlates a detected level to a display brightness according to stored settings in the memory. The conversion process may utilize operator inputs to override default behavior or operate automatically without considering operator inputs. Ultimately, in step 306, the display hardware is controlled according to the brightness setting. The LEDs of a particular display may have their own control circuitry that operates them according to the brightness setting, and an LCD screen or other display may have its own separate control circuitry operating it appropriately.

Conventional powerheads for injectors have included only enough controls to implement a limited amount of functionality as compared to the console of the injector system. The powerhead controls were typically limited to moving the syringe ram and enabling, starting and disabling an injection protocol. The information displayed by the powerhead during an injection was also limited in nature. The console on the other hand has a larger display and more controls that provided additional functionality. Protocol selection and entry, saving and editing injection and syringe parameters, patient contrast volume, injection history, injection phase information and delays, syringe parameters, interface information, instructions and help screens, etc. are all functionality typically provided through the console but not the powerhead.

In contrast to the conventional injector system, as just described, embodiments of the present invention include a powerhead that does not require a console. Through screens on the powerhead an operator is able to control everything involved in an injection sequence. As one advantage of such a system, the up-front cost of the injector without a console is reduced. Also, the ability of the display of the powerhead to display more and better information, help screens and other functions allows an operator to more efficiently operate and to more quickly learn how to operate the powerhead via a touch screen. Instead of the controls on the powerhead being hardwired switched and buttons, the display could be a touch screen that presents a user interface that is easily reconfigurable and more robust.

Figure 4A:
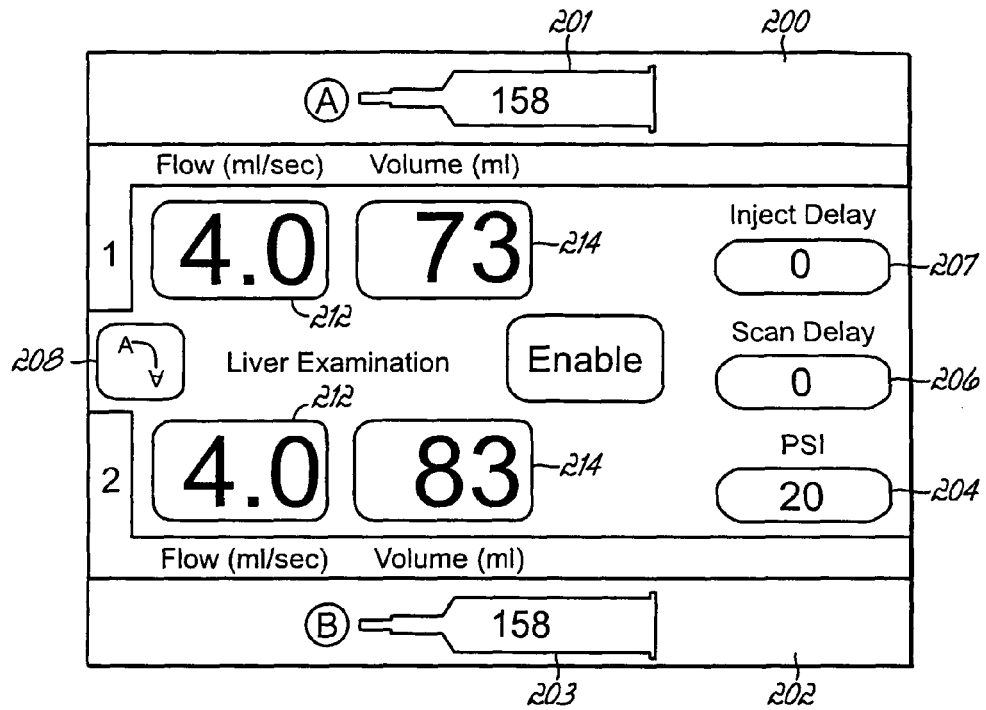

Referring to FIGS. 4A-4F, an injection protocol will be described from the operator's perspective. However, unlike conventional injector systems the interface screens described with respect to these figures are provided by a touch screen display 30 at the powerhead. The main operating screen is illustrated in FIG. 4A. Box 200, which is associated with an iconic representation 201 of the powerhead, identifies the current volume of contrast media in the A syringe. Box 202, which is associated with an iconic representation 203 of the syringe, identifies the current volume of contrast media in the B syringe. Box 204 identifies the pressure limit pre-selected by the operator for the procedure, and box 206 identifies a scan delay (in seconds), which is the delay from the time the operator initiates an injection (either with the hand switch, a key on the console or a button on the powerhead) until the x ray or magnetic scan of the subject should begin (at the end of this delay, a microprocessor within the powerhead produces a tone indicating to the operator that scanning should begin; alternatively, scanning could be automatically initiated by a suitable electrical connection between the scanner and injector). Box 207 identifies an inject delay (in seconds), which is a delay from the time the operator initiates an injection as noted above, until the injection as descried by the protocol will begin, thus allowing time for the scanner to be initiated before flow of contrast. In the illustrated situation, the syringe A contains 158 ml of fluid, 73 ml of which will be used by the currently selected protocol, syringe B contains 158 ml of fluid, 83 ml of which will be used by the currently selected protocol, the pressure limit is 20 psi and there is no scan or inject delay.

Figure 4B:
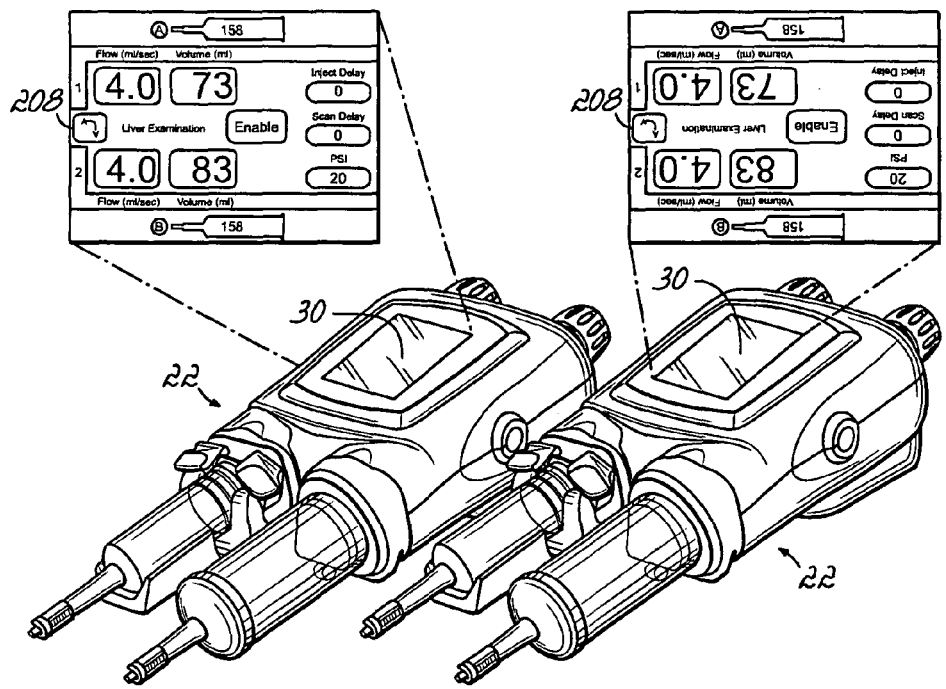
Figure 4C:
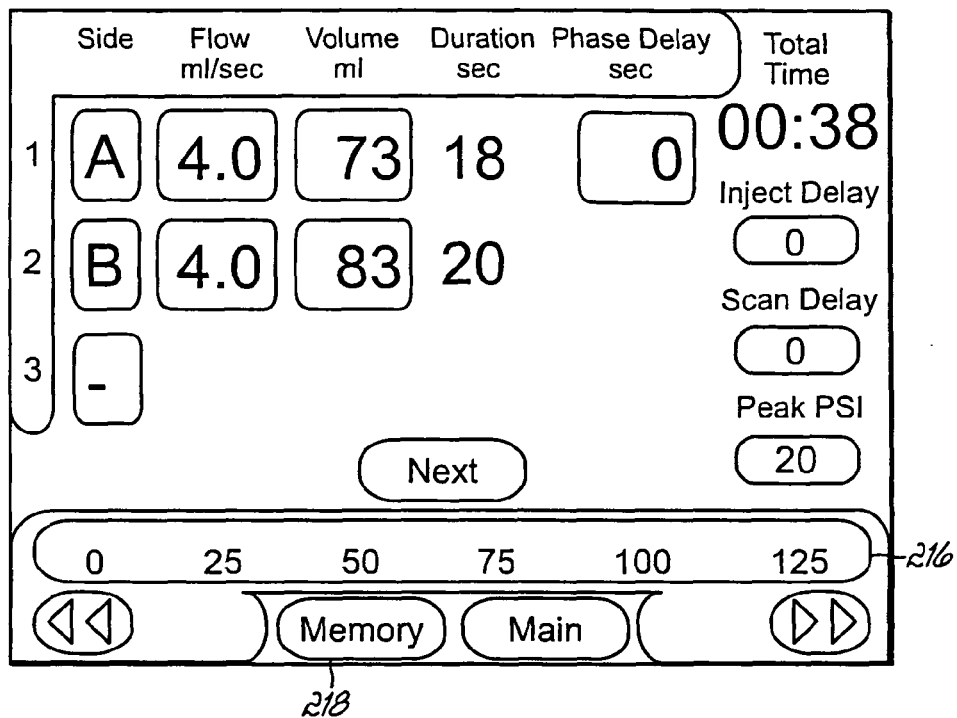

In the display illustrated in FIG. 4A, button 208 may be used to alter the orientation of the display. Specifically, as seen in FIG. 4B, by pressing the screen at this button, the display may be reversed on the screen to thereby facilitate the use of the injector in multiple possible orientations.

As shown in FIG. 4A, a protocol comprises a number of phases; during each phase the injector produces a pre-programmed flow rate to output a pre-programmed total fluid volume. The illustrated protocol has only two phases; however, other protocols which can be selected by the operator have multiple phases. The user can select protocols, enable an injection, and otherwise navigate through display screens by pressing the touch buttons of the display 30.

Regions 212 of the display identify the flow rates for the phases of the current protocol, and regions 214 identify the volumes for those respective phases. The user may alter these parameters by pushing any of these regions, to move thereby to a protocol parameter entry screen, shown in FIG. 4C. On this screen the user may change and store the flow, volume and inject and scan delay values for the current protocol by pressing each of these values as displayed on the screen, and then moving the slide bar control shown in region 216.

From FIG. 4A, the operator may also enter a manual control display by pressing on the iconic representation of a syringe 201 or 203. At the manual control display, shown in FIG. 4D, the operator may manually control plunger movement. At this screen, the iconic representation of the selected syringe in box 200 of FIG. 4A is replaced with a fill-expel bar display 220. By pressing on this fill-expel bar display the motor drive for the selected syringe may be caused to advance or retract thereby to fill or expel fluid from that syringe.

Referring now to FIG. 4E, the display of stored injection protocols can be described. Through the memory button 218 in FIG. 4C, the protocol memory display seen in FIG. 4E may be viewed, where protocols may be stored and retrieved. Protocol memories are known in the art, however, one difficulty with the display of protocols in the prior art has been the limited space available to display a representation of a large number of protocols. For example, as seen in FIG. 4E, only eight protocols can be adequately represented on the display, each associated with a customized named button 222 in the left hand column, and parameters displayed in the right hand column. To overcome this difficulty, in accordance with principles of the present invention, five graphical "tabs" 224 are also provided on the display. Each tab is associated with different set of eight protocol storage locations 222, and the operator may move quickly between the tabs by pressing upon the tabs 224. In this way, forty protocols may be stored and quickly retrieved while continuing to provide sufficient information regarding each protocol on the screen. The tabs 224 may bear numbers or may have user-configurable names as are used with protocols, so that, for example, one tab may contain protocols used with each of several technicians or physicians.

The above description of an interface for an exemplary powerhead identifies a number of specific features; however, the principles of the present invention apply to a variety of other touch-screen features that may also be provided. Indeed, a touch screen provides sufficient flexibility in the interface that certain embodiments of the present invention contemplate providing a complete interface at the powerhead such that a console is no longer needed for a power injection system.

U.S. Pat. No. 5,868,710, commonly assigned to the present assignee, is incorporated by reference in its entirety. That patent discloses a display screen for an injector powerhead that automatically detects the orientation of the powerhead and flips the output of the display screen accordingly so that it is more readily readable to an operator. Embodiments of the present invention advantageously include such functionality for the augmented display screen as described above.

Referring to FIG. 4F, in a further embodiment consistent with principles of the present invention, the display screen 30 may be mounted to powerhead 22 by a swivel mount 238, permitting the screen 30 to be positioned flush with a surface of the injector powerhead 22, or to be tilted from the surface of the powerhead 22 as shown by arrows 240, and optionally subsequently pivoted about mount 238 as shown by arrow 242, thus permitting screen 30 to be optimally positioned to permit control and operation of injector powerhead 22 for any number of various possible injector and operator positions.

Figure 4D:
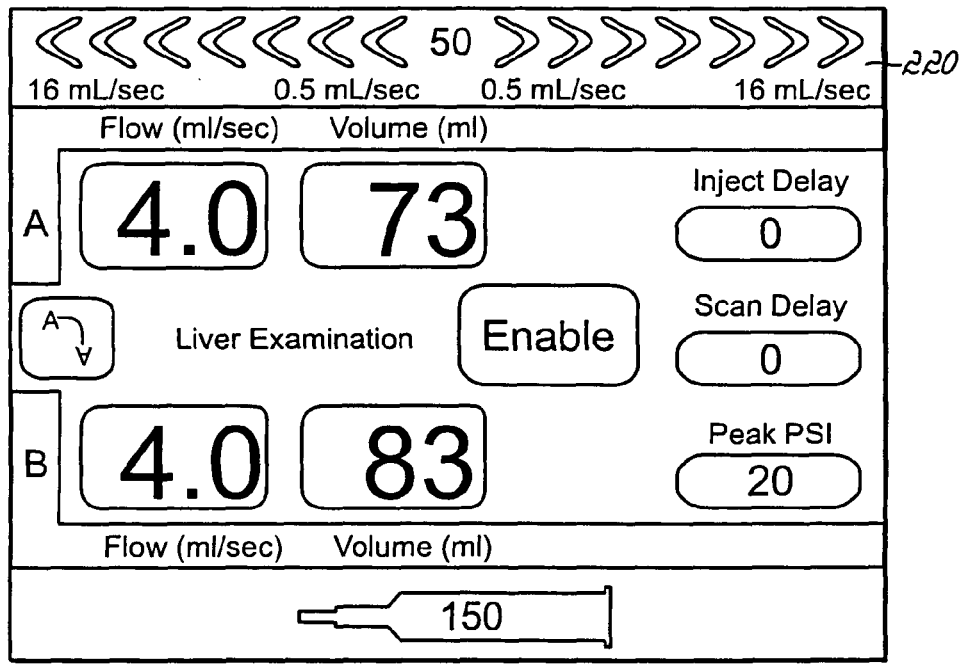

The current orientation of the display as shown in FIG. 4F may be detected by a sensor incorporated within the injector, so as to re-orient the display appropriately as the display is swivelled relative to the injector head. Such a feature may be used in conjunction with the use of a tilt sensor as described in the above-referenced U.S. patent to enable a rich interface selecting an appropriate initial screen display orientation. Furthermore, screen display orientation may be responsive to the current status of the injector in an injection sequence, e.g., one orientation may be used when in a manual control mode as shown in FIG. 4D (when the injector is typically tilted upward for filling) and a second orientation used when performing an injection protocol such as shown in FIG. 4A (when the injector is typically tilted downward for injecting).

It will be appreciated that there are other possibilities for configuring the injector powerhead display in response to injection steps and/or tilt angle of the injector. For example, during an actual injection sequence when the injector is armed, tilted down, and an injection is enabled, the technician using the injector is often in a separated control room far from the injector powerhead. Under such circumstances it may be beneficial to display, in a very large font oriented for an injector tilted downward, the current injector flow rate, volume and/or pressure, potentially together with color coded, blinking or flashing regions or fonts, or graphical iconography, to indicate the injector status in a manner that will be visible by the technician from a great distance, so that the technician may watch the patient during the procedure and still have basic feedback on the operation of the injector without looking to the console.

If the console is included with the contrast media injector system, then the powerhead is a secondary control interface for the contrast media injector system. The computer, memory and executable applications that are typically a part of the console would continue to be a part of the console and the powerhead would simply communicate with the console. If, however, the console were not included in the contrast media injector system then the powerhead or some other component would need to be included that possessed the computational and storage capabilities to provide such functions as on screen textual help, multiple touch screens that are configurable to provide a clear user interface, protocol setting and setup information, etc. that was typically provided by the console.

Turning to a different topic, injector powerheads have conventionally included a single injecting head but dual head injectors are becoming more prevalent as well. Typically, one syringe is used to deliver saline and the other is used to deliver contrast media (although other fluids are used as well). Features that make these injectors safer, easier, and faster to use are desirable; especially those that can be performed automatically by control software within the powerhead.

The dual head injector powerhead 22 with display 30 discussed above, is depicted schematically in FIG. 5 along with tubing and connections thereto. Each syringe 36a, 36b is connected to respective tubing 506, 508 that eventually joins into a common tubing portion 510 that ends at a fitting 512 (e.g., Luer fitting) coupled to a catheter that delivers fluid to a patient.

Figure 6:
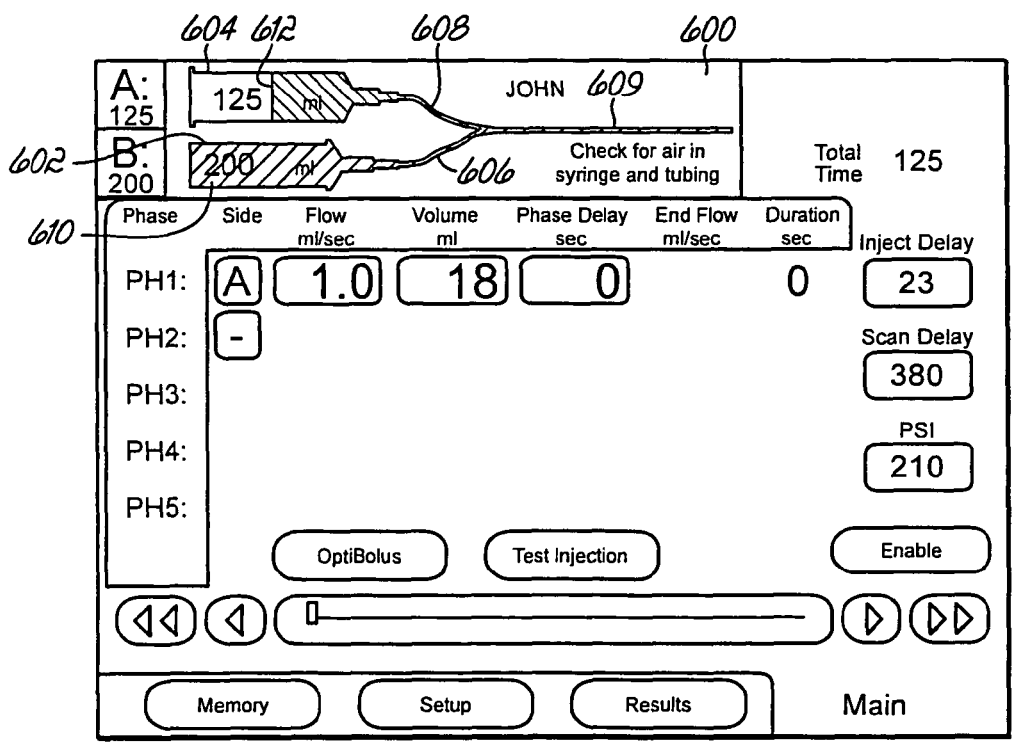

The tubing 506, 508, may be colored to indicate the contents of the tubing or it may be clear. In either case, the display 30 includes graphical information for an operator that indicates the fluid that is being delivered by each syringe 36a, 36b. An exemplary display is depicted in FIG. 6 that may be part of the display screen 30. One graphical image of a syringe 602 and tubing 606 is provided on the left while another graphical image of a syringe 604 and tubing 608 is provided on the right. As shown, a respective fluid 610, 612 is shown in each syringe 602, 604. In particular, as an injection protocol progresses, the display 600 changes to reflect the fluid level changes and to reflect which fluid is being delivered to the patient (portion 609 of FIG. 6).

To assist the operator in recognizing what fluid is being delivered from which syringe, the display 600 color-codes the contents of each syringe and tubing to identify the fluid. For example, a clear color on the display 600 may indicate that air is in a particular syringe and tubing. Coloring the fluid "red" on the display 600 may indicate that contrast media is in that syringe, while a different color (e.g., blue) indicates the presence of saline.

Such a colored display could also be used on a single head injector to indicate the status of different automatic functions. For example, this type of graphical display including color information allows an operator to easily and quickly determine if a syringe is full of air; when an empty syringe and tubing have been properly filled and purged, or when a pre-filled syringe has been purged properly.

It will be noted that dual-head injectors have typically required an a priori selection of saline and contrast locations on the two heads, for example, for consistency with the displays of the injector, a syringe containing saline fluid would be required to be attached to the first side of the injector and a syringe containing contrast media would be required to be attached to the second side of the injector. An aspect of the present invention is to permit configuration of the injector such that displays presented on the injector can be made consistent with any combination of fluid types on the injector. Specifically, an injector in accordance with the present invention permits the operator to define the type of fluid, and color coding thereof, on each of the A and B sides of the injector. Thus, the operator may use the injector with syringes containing fluids of any two arbitrarily selected types, or with fluids of the same types, and correspondingly configure the injector and its displays to match the chosen application. Any arbitrarily selected fluid type may also be used with any arbitrarily selected syringe size. This enables the operator to use either syringe location for any syringe size and any type of fluid, at the operator's discretion, without being subjected to confusingly inconsistent displays from the injector. Alternate color-coded tubing sets may also be provided for matching to the selected injector displays.

Figure 5:
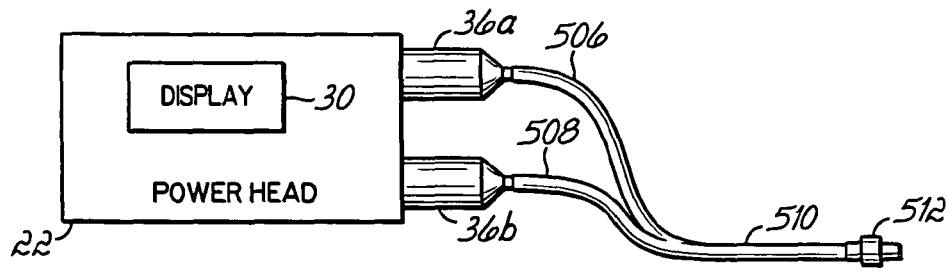
FIGS. 5 and 6 illustrate an exemplary powerhead display screen for a dual head system that correlates tubing color and display icons and colors with each other in accordance with the principles of the present invention.

In the dual head powerhead of FIG. 5, two different fluid tubes are coupled with the injector powerhead 503 but, typically, there is only one fluid entry point at the patient. Thus, the two fluid tubes eventually merge together between the syringes and the patient. In the past, Y-tubing has often been used in which the separate tubes merge relatively near the syringes so that a single fluid tube exists for the majority of the tubing. The inherent elasticity of syringes allows back flow to the non-driven syringe during a pressure injection. Unless precautions are taken with common Y-tubing, a typical injection producing 150 psi will allow about 5 ml of the contents of the driven syringe to be pushed into the undriven side where it will contaminate that side. In the past, check valves have been used to prevent this, but such a solution introduces its own set of problems.

Also, Y-tubing has a lag time between supplying the two different fluids. In other words, the entire contents of the Y-tubing shared portion must be flushed of one fluid before a second fluid can be delivered to the patient. While methods exist for addressing this issue, these methods require additional activity and input by an operator that complicates and lengthens an injection routine.

Figure 8:
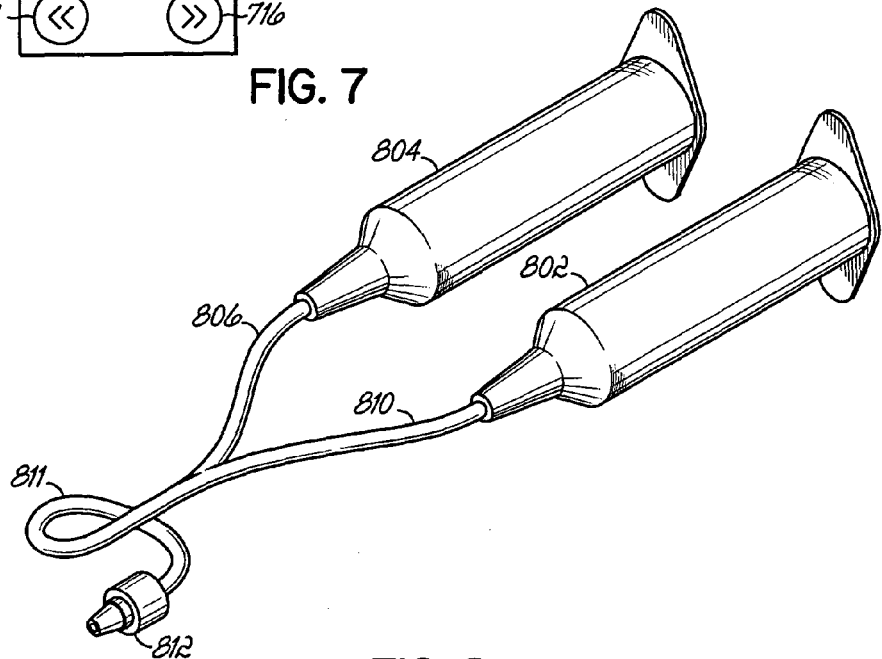
FIG. 8 illustrates exemplary V-tubing to connect a dual injector head system to a patient in accordance with the principles of the present invention.

FIG. 8 depicts a V-tubing arrangement in which the junction between the two tubings is relatively close to the patient's end. Two syringes 802, 804 are used to deliver two different fluids to a patient. The syringe 804 is coupled with an initial portion of tubing 806 and the syringe 802 is coupled with a separate portion of tubing 810. Although these portions of tubing 806, 810 merge externally, they retain separate flow paths through a common portion of tubing 811. The tubing 811 terminates at the patients end with a fitting 812 to deliver one of the fluids.

Figure 9:
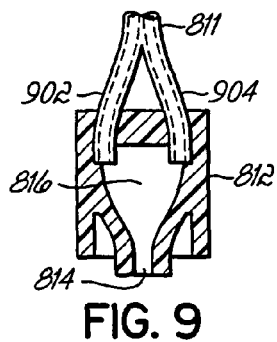
FIG. 9 illustrates an exemplary end fitting for the tubing of FIG. 8.

The cross-section of an exemplary fitting is depicted in FIG. 9. The tubing 811 splits into separate portions 902, 904 that both couple to the fitting 812. In particular, the portions 902, 904 couple to a central cavity 816 such that fluid directed through the tubing sections 902, 904 are delivered to the cavity 816. From the cavity 816, fluid is expelled from the fitting 812 through an opening 814.

Figure 10A:
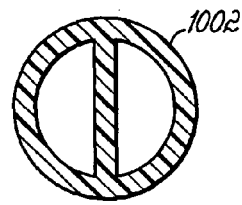
FIG. 10 illustrates an exemplary cross-section of the tubing of FIG. 8.
Figure 10B:
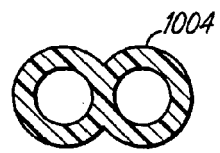

Even though the tubing 811 appears externally to be a single fluid tube, the principles of the present invention maintain the separate fluid paths until the tubing 811 substantially reaches the fitting 811. FIG. 10 depicts exemplary cross-sections that could be used to implement tubing 811. The cross-section 1002 is generally circular in nature with two passageways separated by a vertical wall. The cross-section 1004 is similar to two circular tubes attached along a common side. Each cross section may be formed from co-extruded plastic or by similar means and can be color coded to help identify the intended contents of the tubing.

As mentioned, a typical power injector system includes inherent elasticity due to compression of the syringe plunger and the expansion of the syringe barrel. The shape and size of the plunger affects this amount of elasticity as well. According to certain embodiments of the present invention, the un-driven side of the powerhead may be driven to a sufficient displacement to prevent the movement of fluid into the tubing on the undriven side due to elasticity. The amount of amounts of fluid to drive from an un-driven syringe will be a function of the pressure used on the driven size and the type of syringe in use. In a closed-loop approach, a measure of pressure and/or fluid flow in the undriven sized may be used to perform closed-loop control of the ram on the undriven side to prevent flow into the undriven side due to elasticity. In an open-loop approach, measured values of typical elasticity may be used to drive an appropriate amount based upon the pressure on the driven side. For example, when a 125 ml syringe having a flat plunger face sold by the present assignee is driven at 50 PSI, the undriven side should be driven approximately 1.72 ml to compensate for movement of fluid due to elasticity. With this syringe, at 100 PSI, the driven amount is 2.28 ml, at 150 PSI, 3.45 ml, at 200 PSI, 4.32 ml, at 250 PSI, 5.37 ml, and at 300 PSI, 6.78 ml. Other syringes will have other characteristic values at various pressures. In a combined open/closed loop approach, the initial displacement applied to the undriven side upon initiation of the injection may be obtained from measured typical values, after which a closed-loop control may be initiated to maintain an equilibrated pressure between the driven and undriven sides and/or zero flow rate on the undriven side.

Previous injector powerheads for contrast media injectors have included mechanisms to move the motor powered syringe ram back and forth automatically. These mechanisms have included levers, membrane key pads, push button or toggle switches, magnets and Hall-effect sensors, etc. In all such instances, though, these mechanism were part of the powerhead of the injector.

Embodiments of the present invention relate to a remote control powerhead in which the control means for effecting movement of the syringe ram is locate remotely from the powerhead. Such a remote control will allow an operator greater flexibility in location during certain injector operations and protocols.

Figure 7:
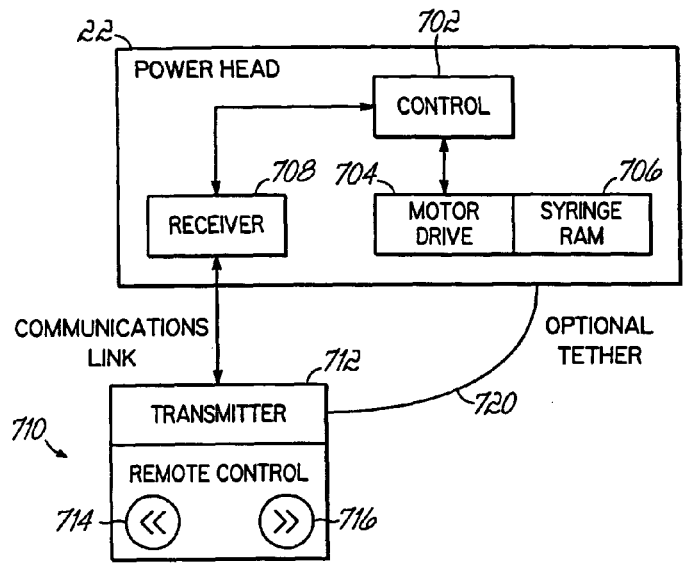
FIG. 7 illustrates a remote controlled powerhead in accordance with the principles of the present invention.

FIG. 7 illustrates one simple remote control 710 that is sized to fit in an operator's hand. The remote control emits a signal from a transmitter 712 that is received at a receiver 708 at the powerhead. Within the powerhead, the signal is converted for use by the motor control circuitry 702 to effect movement of the syringe ram 706 through the motor drive 704. The motor drive 704 and syringe ram 706 operate similar to conventional powerheads except that in addition to receiving input from local controls, the input from the receiver 708 is considered as well. The exemplary remote control 710 includes two buttons 714, 716. One button 714 extends the ram 706 towards the front of the syringe and the other button 716 retracts the ram 706 from the front of the syringe. This particular remote control 710 permits one-handed operation because of its size and button placement.

One of ordinary skill will recognize that such a remote control 710 can include a variety of functions, have a variety of physical form factors, and include various numbers of buttons and knobs, without departing from the scope of the present invention. For example, a potentiometer (linear or rotary) may be used to remotely control the ram movement at a fixed speed. Alternatively, a pressure sensitive switch may be utilized that permits control of the ram movement but changes its speed depending on the pressure supplied.

The frequency at which the remote control and the powerhead communicate is not a material constraint of the present invention which explicitly contemplates UHF, VHF, RF, infrared, ultrasonic, etc. as exemplary communication modes. Because the remote control may have a tendency to be separated from the general vicinity of the powerhead, a physical tether 720 may be provided that limits the removal of the remote control from the powerhead. Accordingly, this tether may also act as a communications path in certain embodiments such that the remote control is not a wireless device but is coupled to the powerhead via a physical cable.

During venous procedures utilizing power injectors, the contrast media or imaging agent is sometimes unintentionally injected into the tissue surrounding a patient's vein. This is generally referred to as extravasation and is considered a hazard. It is commonly caused by the operator missing the patient's vein entirely while inserting a catheter; piercing through the vein into surrounding tissue; or injecting at a flow rate that punctures the wall of the vein.

There are common techniques used by operators to detect or prevent extravasation but these are not always 100% effective. When using a dual head injector, one common technique is to perform a patency test by first injecting saline into a patient's vein while observing for skin swelling. This may be done manually or as part of a stored protocol. While effective in some cases, the saline may not be injected at a flow rate and volume that adequately simulates the injection protocol. Thus, the actual imaging agent injection may extravasate even if the saline injection did not.

Embodiments of the present invention relate to a dual head power injector that includes in its software, one or more routines that assist an operator in selecting an optimum flow rate and volume during the saline injection test portion of a patency test. The patency test interface screen will suggest to the operator flow rate and/or volume values that are based on the selected protocol that provide a simulation that is substantially similar imaging injection that is to follow. This additional functionality may be included via a separate dedicated display on the powerhead, or console, or may be one of the many menu screens typically presented to an operator through the general interface screen. Also, the software may automatically set the flow rate and volume or permit the user to set, or modify, the values after seeing the suggested values.

Certain safeguards may be included such that a patency check may not be performed until a protocol is enabled or until a manual purge has been completed. Also, the patency check may include a verification that enough saline remains available before proceeding with the patency check.

Figure 11:
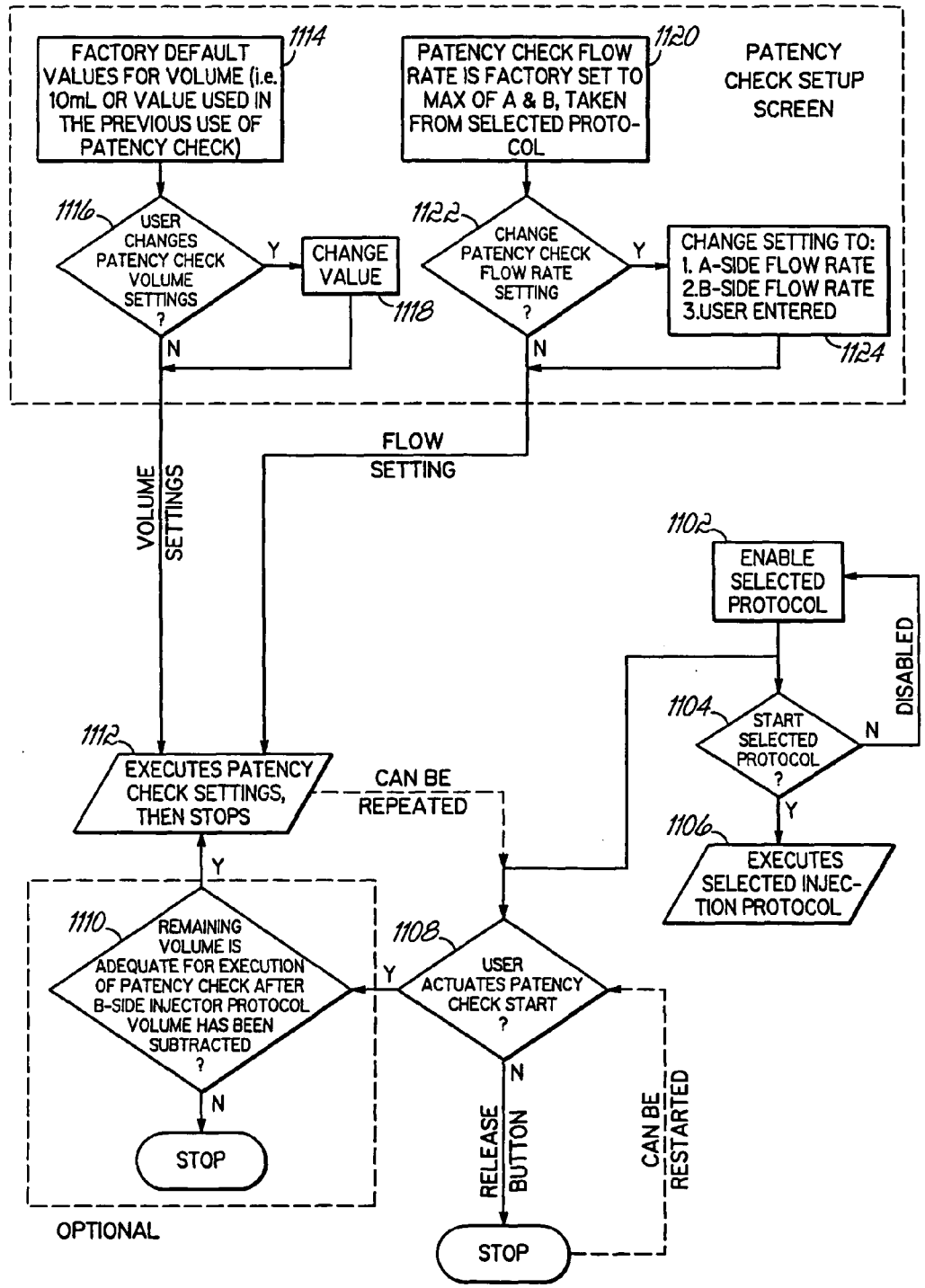
FIG. 11 depicts a flow chart of an exemplary method to perform a patency check with a dual head injector system.

In general, the principles of the present invention can be implemented according to an exemplary algorithm depicted in the flowchart of FIG. 11. In step 1102 an injection protocol is selected and enabled. Before the protocol is performed, however, the operator may want to perform a patency check, and activates the patency check (step 1108). In an exemplary embodiment, the user indicates desire to perform a patency check by pressing and holding the expel button for the saline syringe for a given period of time, although numerous other interface methodologies may be used to permit the user to initiate a patency check. As shown in the flow chart, the specific methodology discussed here requires that the operator press a button for more than the threshold time, thus ensuring that a patency check is not unintentionally initiated. If the button is released too early, no patency check is performed, but may be re-initiated as illustrated at step 1108.

In the described embodiment, the software performs an optional check in step 1110 to determine if adequate fluid exists to perform the patency check and the selected protocol. If there is not adequate fluid, the process stops. However, if there is sufficient fluid, then the patency check may be executed in step 1112.

Based on the selected protocol, an operator is presented interface options to set up the patency check. These options derive from the existing protocol or from settings made by the user. As seen at step 1114, a volume for the patency check is derived from a factory default, or a historical volume used for previous patency checks. As shown at step 1116, the user has the opportunity to change the volume if desired. If, so, then the volume value is changed in step 1118. As seen at step 1120, a flow rate is also selected for the patency check. Again, this could be based on the protocol, a default value or historical data. In the described embodiment, the default flow rate is selected to be the maximum flow rate on the "A" or "B" sides of the injector, so that the patency check verifies the lack of extravasation at the largest flow rate that will be required. Here again, the user is provided the option of changing the patency check derivation in step 1122—if desired the user may choose the "A" side flow rate or maximum "A" side flow rate, or the "B" side flow rate or maximum "B" side flow rate, in step 1124.

Once the user has been presented with patency check settings (e.g., in a setup screen displayed immediately after step 1110), the user may execute the patency check in step 1112. Assuming no extravasation is evident, the operator would typically proceed to enable the protocol in step 1102, at which point the injector awaits a "start" indication from the operator in step 1104, upon which the protocol is executed in step 1106. If there is extravasation seen during the patency check, this may be remedied, and another patency check performed.

Figure 12:
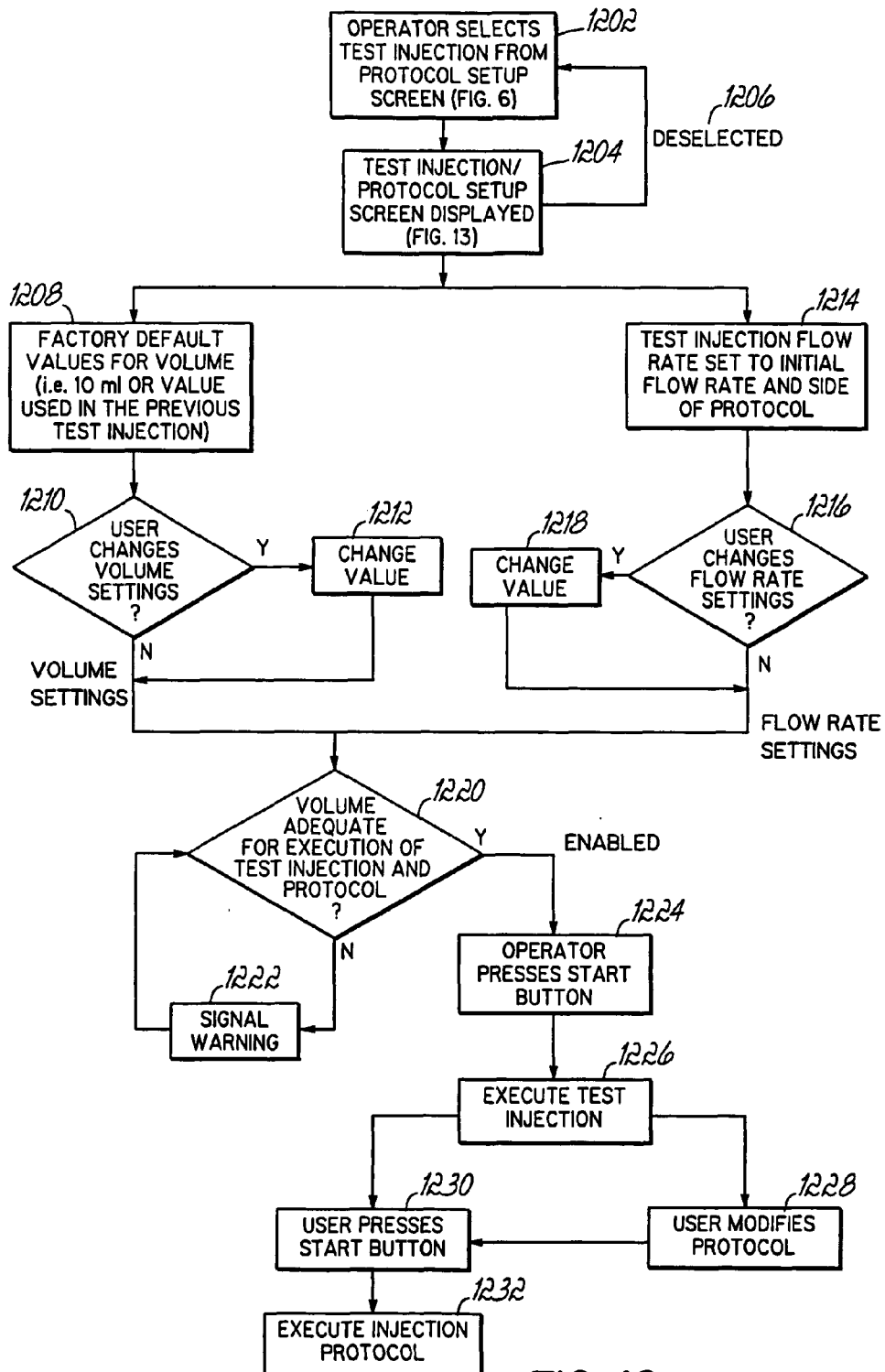
FIG. 12 depicts a flow chart of an exemplary method to perform a test injection with an injector system.
Figure 13:
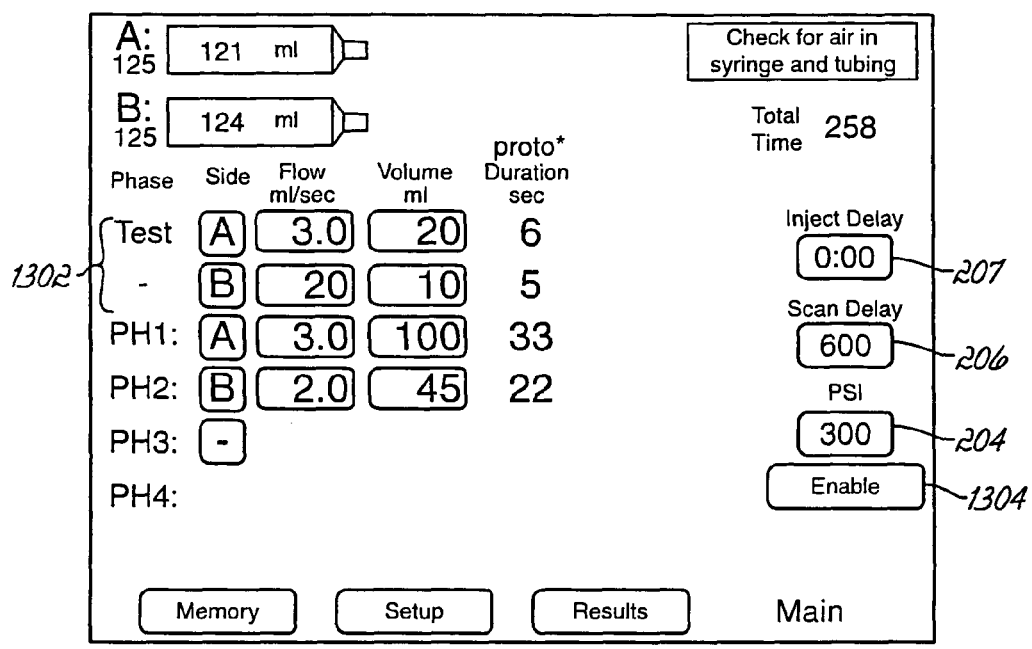
FIG. 13 depicts an exemplary display screen for a dual head injector system used to perform a test injection method.

Referring now to FIG. 12, a test injection methodology can be described. To perform a test injection, in step 1202 the operator selects a test injection when configuring an injection protocol, such as by depressing the "test injection" key in the protocol setup screen shown in FIG. 6. Once a test injection is selected, the test injection/protocol setup screen is displayed, as shown in FIG. 13. On that screen, it can be seen that in addition to the injection protocol parameters displayed as shown in FIG. 6, test injection parameters are displayed in an area 1302. These parameters include parameters identifying the flow rate and total volume of a test injection.

As seen in FIG. 12, the values for the flow rate and volume of a test injection are generated using the stored information and protocol parameters that have already been set by the user. Specifically, as seen at 1208, a factory default value (e.g., 10 ml) may be initially used as the volume of a test injection, or the volume used in a prior test injection may be used. The volume setting created is a default, but can be changed. As seen in FIG. 13 the test injection flow rate and volume settings are shown in buttons on the screen, which may be touched to enable adjustment with a slider bar or other graphical control as is shown in FIG. 6. Thus, in step 1210 of FIG. 12 the user may take action to change the volume settings and in step 1212, make a desired change to generate the final volume settings for the test injection.

Similarly, in step 1214, a default flow rate is created for the test injection based upon the initial flow rate and side ("A" or "B") used in the already programmed protocol. These values are defaults and, as before, in step 1216 the user may take action to change the flow rate in step 1218. After making changes or accepting the defaults, the flow rate settings are determined.

In addition to the above adjustments, the user may change the head used by touching the button in the "Side" column on the graphical display, as is done in the interface of FIG. 6 when a test injection is not selected.

Initially, a test injection may include only injection from one side of the injector, e.g., the "A" side or a side that has been identified as carrying contrast media. However, a test injection may also use both sides, e.g., to inject a bolus of contrast media followed by a saline flush so as to create a "packet" of contrast media surrounded by saline fluid. Or the test injection may be done only with contrast media, at the operator's discretion. Whether both sides are used may be determined from whether both sides are used in the subsequent protocol, and/or on various default parameters. The injector may include default setting screens for identifying the default use of injection heads as well as methods for deriving volumes and/or flow rates from a current protocol or prior test injections, allowing operator configuration of the injector's behavior.

After the parameters of a test injection are set in the manner noted above, in step 1220 the injector evaluates those parameters in an optional step to determine whether there is adequate volume for execution of both the test injection and the subsequent protocol. If there is not adequate volume then in step 1222 the operator may be warned of the insufficiency, for example by indicating in a red color or by blinking colors, or both, of the part of the injection for which there will be insufficient volume of fluid available. This warning is particularly useful in that it avoids a circumstance where the operator must return to the imaging room after a test injection or a partially completed injection, to refill syringes and remove air, potentially wasting contrast media and substantial time in re-work. In a circumstance of insufficient volume, the injector may prevent the test injection, or may allow operator override of the warning, as may be suitable for a given clinical setting. The response of the injector may also be different based upon whether there is inadequate contrast media (which is more likely to have adverse effects on imaging) or inadequate saline (which is less likely to have such effects).

After passing through the optional step 1220, the user may enable the injector by pressing the enable key 1304 shown in FIG. 13 (if not previously enabled), which leads to step 1224 shown in FIG. 12. At this point, the test injection may be initiated by the operator pressing the start button in step 1224. When the start button is pressed, then in step 1226 the test injection step(s) are executed as set forth on the setup screen shown in FIG. 13. Thereafter, the operator evaluates the test injection and, for example, the quality of imaging achieved with the set flow rate and/or the scan delay from the time of the injection to the appearance of contrast media on the scanner, and in step 1228 may adjust injection parameters for the injection protocol in response. If there is a pressure limit hit during the test injection, then the injector may disable, and provide a warning that a pressure limit was hit, so that the operator is spurred to make modifications through step 1228 before re-enabling the injection prior to execution of the protocol. Thereafter, the user may depress the start button in step 1230 to cause the injector to execute the injection protocol in step 1232.

It will be appreciated that one use of the test injection may be to identify the time required for contrast media to reach a particular part of the patient's body where it can be effectively imaged, so that, for example, the technician may set a scan delay time defining when scanning should commence after an injection has begun. To facilitate this activity by the technician, an injector in accordance with principles of the present invention may incorporate a number of features that work with the test injection function to ensure an accurate scan delay calculation.

First, the injector may be usable to compute a scan delay time from (a.) the reconstruction time of the scanner being used and (b.) the observed time delay from the beginning of injection to the appearance of contrast media on the scanner display. The reconstruction time of the scanner must be subtracted from the observed time delay to identify an accurate scan delay time, since observation of contrast on the scanner will be after contrast has actually arrived at the location seen on the screen, due to reconstruction delay. Thus, to facilitate the determination of an accurate scan delay, the injector may facilitate computation of the difference of the observed time difference and scanner reconstruction time. An injector configured to compute this difference may also be configured to assist in measuring the time delay between the start of injection and observation of contrast, for example by measuring an elapsed time between the start of an injection and a input by the technician that contrast is being observed on the scanner display.

Second, the injector may assist in the repeatability of injection activity by including functionality to return the state of the Y or V tubing connected to the injector to a predetermined state. For example, the desired initial state prior to an injection may be that the tubing, through to the injection site, be filled with saline. This initial state is a potentially important part of the timing that will be achieved in an injection, as the initial flow of contrast into the injection site may be delayed by several seconds corresponding to the time to flush saline out of the tubing and contrast into the tubing. Alternatively, the initial state prior to an injection may be that the tubing is filled with contrast, or some part of the tubing has saline and some part has contrast. Those initial conditions will have different corresponding behaviors in the timing of the start of an injection.

An injection in accord with principles of the present invention may contain a feature in which the main single line section of the Y or V tubing is prefilled with contrast, saline, or any predetermined combination of the two, according to the settings of the injector and/or preferences of the operator. To implement this feature the injector would contain information about the specific tubing used, the volume of tubing after the joint to a single tube, as well as the desired initial condition. If the main single line section is no greater than 10 ml in capacity, then an initial fill of that section by a desired fluid may be assured by a push of 10 ml of the desired fluid as a final step prior to initiation of the injection.

An injector implementing this initial condition function may follow a test injection as set forth in FIG. 12 by such a single push of saline or contrast, as desired, to return the injector to the desired initial condition. Thus, for example, if a test injection involves a final step that is a contrast injection, and the desired initial condition is to have the single main line flushed with saline, then after the test injection the injector would automatically push saline to flush the single main line and return the injector to the desired initial state. The obverse activity could be performed where a test injection has a final step that is a saline injection and the desired initial condition is to fill the single main line with contrast.

It will be further appreciated that the desired initial condition for an injection may be a parameter or may be deduced from the nature of the protocol requested; e.g., in one embodiment it might be assumed that if the first injection step is contrast that the desired initial condition is to have the single main line filled with saline fluid, and so proceed at the initialization of a test injection as well as in the initialization of the injector after the test injection and prior to execution of the programmed protocol.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A contrast media injector system comprising:
a powerhead including a display screen;
the powerhead configured to control injection of a fluid from within a fluid container coupled thereto to a patient through tubing connected to the fluid container;
a first iconic graphical element within the display screen representing the fluid container and the fluid therein, wherein a color of the graphical element is selected based on an identity of the fluid; and
a second iconic graphical element within the display screen representing the tubing and the fluid therein, wherein a color of the second iconic graphical element is substantially identical to the color of the first iconic graphical element, and wherein the second iconic graphical element extends from the first iconic graphical element on the display screen.

2. The system of claim 1, wherein a color of the first iconic graphical element representing the fluid container and the fluid is yellow if the fluid is saline.

3. The system of claim 1, wherein a color of the first iconic graphical element representing the fluid container and the fluid is purple if the fluid is contrast media.

4. The system of claim 1, wherein a color of the first iconic graphical element representing the fluid container and the fluid is black if the fluid is air.

5. The system of claim 1, wherein the first iconic graphical element representing the fluid container and the fluid and the second iconic graphical element representing the tubing indicate a level of the fluid within the fluid container and connected tubing, respectively.

6. The system of claim 1, wherein the powerhead is a dual head powerhead and the display screen includes the first iconic graphical element for a first syringe connected thereto and a third iconic graphical element for a second syringe connected thereto, wherein a respective color for each of the first and third iconic graphical elements is dependent on a respective fluid associated with each of the first and second syringes.

7. The system of claim 6, further comprising respective first and second tubing connected to the first and second syringes, the display screen including the second iconic graphical element for the first tubing and a fourth iconic graphical element for the second tubing, wherein the second and fourth graphical elements are colored substantially similar to the color of the first and third iconic graphical elements, respectively, and wherein the fourth iconic graphical element extends from the second iconic graphical element on the display screen.

\* \* \* \* \*